United States Patent [19]

Fründel

[11] 4,123,665

[45] Oct. 31, 1978

[54] ARRANGEMENT FOR DETERMINING THE DENSITY OF NATURAL FOG IN THE ATMOSPHERE

[76] Inventor: Frank Fründel, Glockenacker 2, Zurich, Switzerland

[21] Appl. No.: 712,956

[22] Filed: Aug. 9, 1976

Related U.S. Application Data

[60] Continuation of Ser. No. 533,171, Dec. 16, 1974, abandoned, which is a continuation of Ser. No. 433,445, Jan. 15, 1974, abandoned, which is a division of Ser. No. 266,441, Jun. 26, 1972, Pat. No. 3,808,430, which is a continuation of Ser. No. 498,195, Oct. 4, 1965, Pat. No. 3,672,775, which is a continuation of Ser. No. 194,235, May 14, 1962, abandoned.

[30] Foreign Application Priority Data

May 16, 1961 [DE] Fed. Rep. of Germany ........... 33930

[51] Int. Cl.$^2$ .......................................... G01N 21/28
[52] U.S. Cl. .................................. 250/565; 356/103
[58] Field of Search .............. 356/207, 103, 102, 237, 356/; 250/236, 237 R, 209, 226, 573, 574, 204, 207

[56] References Cited

U.S. PATENT DOCUMENTS

| 2,182,987 | 12/1939 | Hopkins | 250/237 R |
|---|---|---|---|
| 2,463,119 | 3/1949 | Pyle et al. | 250/207 |
| 2,626,361 | 1/1953 | Martine | 356/207 |
| 2,700,916 | 1/1955 | Muirhead | 250/237 R |
| 2,806,401 | 9/1957 | Demuth et al. | 356/237 |
| 2,907,889 | 10/1959 | De Lisle Nichols et al. | 250/236 |

OTHER PUBLICATIONS

Horman, Melvin H., *The Determination of Atmospheric Transmissivity By Backscatter From a Pulsed Light Separated System*, Motorola Report No. RL-3828-2, Oct. 1958, pp. 4, 12, and 14.

Horman, Melvin H., *Measurement of Atmospheric Transmission Using Backscatter From a Pulsed Light Separated System*, ASTIA Document No. 217,614, Motorola Report No. RLF-3828-3, Jun. 1959, pp. viii, 7, 12, 15, 16, 19, 21, 22, 26, 27, 81 and 82.

*Electrical Record*, Mar. 1930, p. 25, article entitled, "Chalk One Up for Lindy."

*Primary Examiner*—Alfred E. Smith
*Assistant Examiner*—T. N. Grigsby
*Attorney, Agent, or Firm*—Michael J. Striker

[57] ABSTRACT

An arrangement for determining the density of natural fog in the atmosphere in which a spark lamp serving also as a flashing beacon projects a beam of light composed of consecutive pulses through the fog laden atmosphere so as to scatter part of the light to thus form consecutive pulses of scattered light in a defined region of the path of the light beam, the intensity of which is proportional to the density of the fog in this region, and in which light pulse receiver means are constructed and arranged relative to said region so as to receive only the scattered light pulses which are measured by the receiver means to thereby indicate the density of fog in the aforementioned region.

8 Claims, 3 Drawing Figures

ARRANGEMENT FOR DETERMINING THE DENSITY OF NATURAL FOG IN THE ATMOSPHERE

CROSS REFERENCE TO RELATED APPLICATIONS

The present application is a continuation of my copending application Ser. No. 533,171, filed Dec. 16, 1974 and now abandoned. Application Ser. No. 533,171 was a continuation of my prior copending application Ser. No. 433,445, filed Jan. 15, 1974 and now abandoned. Application Ser. No. 433,445 was a division of my prior copending application Ser. No. 266,441, filed on June 26, 1972 and now issued as U.S. Pat. No. 3,808,430. Application 266,441 in turn was a continuation of my prior copending application Ser. No. 498,195, filed Oct. 4, 1965 and now issued as U.S. Pat. No. 3,672,775. Application 498,195 in turn was a continuation of my prior copending application Ser. No. 194,235, filed May 14, 1962 and now abandoned.

The present invention concerns an arrangement for determining the range of visibility across a light-transmissive medium which may be gaseous or liquid. In a particularly advantageous application of the invention the above mentioned arrangement constitutes a fog warning arrangement furnishing an electric signal or the like when the visibility in a certain area is reduced for instance by fog to a certain range in which case a warning signal or indication is desired, in accordance with predetermined standards. Of course, instead of giving a warning signal the arrangement according to the invention may be used simply for measuring and/or recording variations of visibility.

In order to be able to carry out a determination of an existing range of visibility not only at night but also at day time it has been found advisable and necessary to operate with light pulses of very high intensity because such light pulses can be observed and registered also under daylight conditions.

It has been proposed previously to determine a range of visibility across a light-transmissive medium or the absorption of light through such a medium by emitting from a transmitter light pulses and by receiving such light pulses at a receiver station across such medium and to use the indication of the intensity of light pulses received at a receiver station as an indication of the visibility or light absorption through the medium existing between the transmitter and the receiver station. However, local conditions are frequently such that a suitable base distance between transmitter and receiver station for receiving the direct light rays from the transmitter station cannot be established.

It is therefore one object of the present invention to provide an arrangement for determining the range of visibility across a light transmissive medium in such a manner that the existing range of visibility is determined by sampling a comparatively small volume of the medium by means of a transmitter and a receiver station separated from each other only a comparatively small distance.

It is a further object of this invention to provide for an arrangement of the type set forth which eliminates the utilization of direct light rays between the transmitter and receiver station.

It is still another object of this invention to provide for an arrangement as mentioned above which eliminates the effect of general daylight illumination surrounding the arrangement so that the receiver station responds only to light pulses emanating from the transmitter station.

With the above objects in mind the invention includes an arrangement for determining the range of visibility across a light-transmissive medium, comprising, in combination, light pulse transmitter means; and light pulse receiver means so constructed and arranged relative to said light pulse transmitter means that pulses of direct light rays emanating from said transmitter means are prevented from reaching said receiver means, and that only light pulses emitted from said transmitter means and scattered by visibility reducing particles that may exist in said medium are received by said receiver means, the latter being capable of delivering an electrical signal in a predetermined proportion to the intensity of pulses of scattered light received by said receiver means and thereby quantitatively indicating a reduction of the range of visibility due to the presence of visibility reducing particles in said medium as compared with the range of visibility existing in the absence of such particles.

It will be understood readily that the greater is the density of e.g. fog in a sample volume of air in the area of the transmitter and receiver stations the greater will be the amount of light scattered by the fog and reflected or deflected into the receiver station. Assuming a constant amplitude of the light pulses emitted from the transmitter station there is a strict interdependence between the existing range of visibility and the amplitude of the light pulse received by the receiver station. In other words, the product of the unit of visibility range and of the voltage amplitude of an electrical signal produced by a receiver including photo-responsive means having a linear characteristic remains a constant. For instance, if the visibility decreases to one half of a previously existing value then the resulting signal voltage at the receiver would double its value as compared with the previously existing signal value.

In evaluating the advantages of the invention it should be borne in mind that in a conventional system utilizing the direct light rays between transmitter and receiver stations separated from each other by a substantial distance the intensity of the light impinging on the receiver station is greatly reduced in the case of considerable light absorption through fog or other particles present in the air or other medium between the stations because a great portion of the emitted light is scattered. At the same time a substantial amount of scattered light also impinges on the receiver whereby the noise level (conventionally called "white noise") is raised substantially so as to make the detection of the actual signal very difficult. If in such a case one would attempt to eliminate the effects of scattered light very complicated means would have to be employed, but nevertheless the quality of the received signals remains unsatisfactory. All these difficulties are entirely eliminated according to the invention by relying not on the direct light rays but only on scatter light produced by a comparatively small volume of the medium containing scattering particles and existing in the vicinity of the transmitter and receiver stations.

Of course, since only a sample volume of the medium is utilized in determining a range of visibility across a larger body of said medium it is necessary to take precautions that a representative sample of that larger body of the medium is present in the area or vicinity of the transmitter and receiver stations. Therefore, these stations should be freely accessible for instance to the surrounding air, and in certain cases it may be advisable to provide for a fan or similar means for moving a representative amount of said larger body of the medium into the area or vicinity of the transmitter and receiver stations.

It is to be understood that the arrangement according to the invention can be used with similar advantage, although with obvious adaptations, both for determining a range of visibility across gaseous medium as well as for indicating or measuring the turbidity of a liquid.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

Figure 1:
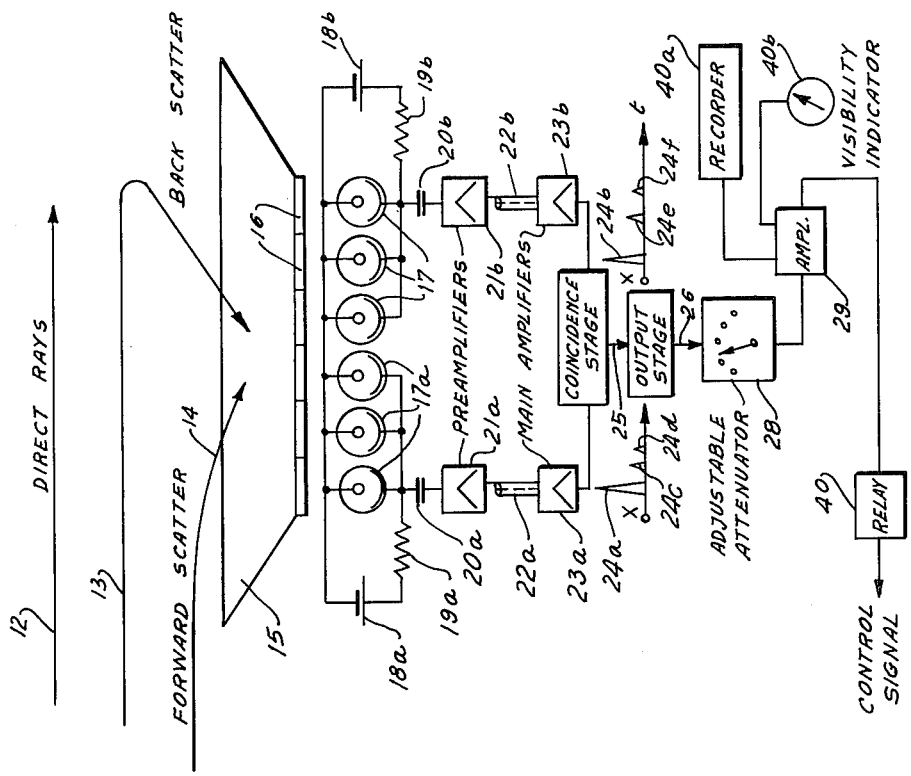
FIG. 1 illustrates diagrammatically an embodiment of the invention comprising a transmitter and receiver station.
Figure 1:
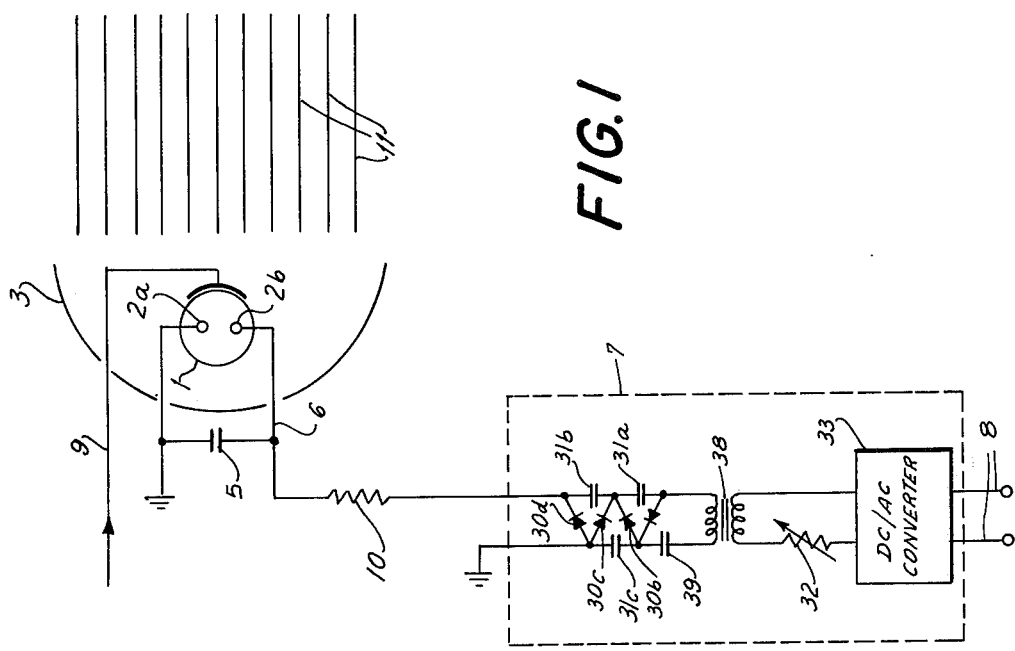

Referring now to FIG. 1, the transmitter station comprises a spark discharge lamp 1 of conventional type having two spark electrodes 2a and 2b and an igniting electrode 4. The lamp 1 is located in the focal point of a reflector 3 e.g. of parabolic form for reflecting light pulses emanating from the lamp 1 in a predetermined direction indicated by line 12. Of course, instead of a reflector as mentioned above and arranged behind the lamp 1 a suitable lens could be arranged for the same effect in front of the lamp 1. The lamp 1 is operated by discharges from a capacitor 5 through the connecting lines 6 in a well known manner. Circuit arrangements for producing spark discharges of uniform light amplitude are known per se and do not constitute part of the present invention. Also, the spark discharge lamp 1 is being mentioned here only by way of example because other devices for generating light pulses of uniform amplitude may be used with equal effect. Preferably, in the desired example the self-inductance of the discharge circuit of the capacitor 5 should be so dimensioned that the energy consumed in the spark discharge is in a fixed proportion to the aperiodic resistance of the discharge circuit. The capacitor itself should have as small as possible inductance. The same applies to the connections 6. The capacitor 5 is chargeable with sufficient rapidity by a charge generator 7. If desired, instead of a single capacitor 5, two capacitors in parallel arrangement may be used. Preferably, the generator 7 may contain a cascade circuit arrangement as illustrated. This circuit is to be supplied with alternating current. Therefore, depending upon whether a supply of direct current or alternating current is available a transistorized converter 33 may be used for feeding alternating current to the primary winding of a transformer 38. A variable resistor 32 may be provided for limiting the current supplied to the transformer 38. The converter 33 may be so constructed that upon being supplied with direct current at 12 volts it delivers an alternating current at 500 volts. The alternating current delivered by the secondary winding of the transformer 38 is applied via a current limiting capacitor 39 to a plurality of rectifiers 30a, 30b, 30c and 30d whereby the capacitors 31a, 31b and 31c connected in cascade as shown are charged. The emission of light pulses may be controlled by introducing igniting pulses through line 9.

Instead of causing the emission of light pulses arbitrarily by injection of igniting pulses the lamp 1 may also be operated without such igniting pulses so as to produce a periodic pulse sequence in which case the resistor 10 in the charging circuit would determine the frequency of the light pulses. This method is satisfactory if it is only desired to produce such a continuous sequence of light pulses by alternately switching the lamp 1 on and off.

Light pulses produced in this manner are barely visible to the human eye, yet completely satisfactory for the purpose of the arrangement according to the invention.

Since in the embodiment according to FIG. 1 only unidirectional radiation from the lamp 1 is desired it is advisable to provide in front of the lamp 1 or of the reflector 3 or the like a system of ducts 11 arranged in honeycomb fashion and parallel with each other in the direction of the above mentioned arrow or line 12. Hereby scattering of light in the immediate vicinity of the lamp 1 is prevented.

The receiver portion of the arrangement according to FIG. 1 comprises at its input side a protective screen or blind 15 which is oriented to face in a direction substantially at 90° with respect to the above mentioned direction 12 of the rays emanating directly from the transmitter station. As can be seen from FIG. 1 the member 15 has an opening which permits entrance of light pulses furnished by the lamp 1 and scattered either in forward direction as indicated diagrammatically by the line and arrow 14 or of scattered light reflected backwards as diagrammatically indicated by the line and arrow 13. On the other hand, direct light rays 12 are prevented from reaching the receiver arrangement. For the purposes of this description the term "forward scatter" includes also sideways scatter. It is easy to arrange matters in such manner that scatter in directions between 10° and 170° with respect to the direction 12 will be received by the receiver arrangement. Due to the scatter characteristics of air, dust, fog and other particles, a cosine law function is provided for in the photocell portion of the receiver arrangement described further below. The blind 15 prevents light from other sources located laterally thereof from entering the receiver arrangement.

By arranging the receiver arrangement at a comparatively short distance from the transmitter arrangement described above it is easy to provide for a sample volume of air or another medium comprising about 28 cubic feet to be used as a representative sample of the medium the visibility whereof is to be determined.

At the rear end of the protective blind 15 a layer of filters 16 may be provided which may serve as an additional means for eliminating the influence of foreign sources of light. The receiver is equipped with at least one, but preferably with a plurality of photocells responding to light radiation entering through the protective blind 15 and the set of filters 16. The filters 16 may be of such a nature that substantially only white is applied to the photocells, but the filters may also be of a different nature so as to permit the passage of only light of a particular color or even only of ultraviolet light. If the filter set 16 consists of so-called neutral filters, then it will only serve to attentuate bright daylight in order to prevent an overloading of the photocells. If the filter set 16 permits only the passage of ultraviolet light and if the light pulses emitted by the transmitter contain a substantial amount or consists only of ultraviolet light then the advantage is obtained that the receiver will be particularly sensitive because ultraviolet light is subjected to a particularly intensive scattering.

In a particularly advantageous embodiment of the invention as illustrated by FIG. 1 first group of photocells 17a and a second group 17 are arranged in the area behind the filter set 16. The two groups of photocells 17a and 17 cooperate with a coincidence stage 24. For practical purposes the number of photocells in each group should be equal to each other. The number of photocells in each group should be chosen so as to obtain a substantial output signal therefrom. As shown in FIG. 1 each group is supplied with energy from a battery 18a and 18b, respectively, via load resistors 19a and 19b, respectively. Of course, both groups may also be supplied from one common source of energy. When a pulse of scattered light impinges on one or the other group of photocells the corresponding output pulse generates a voltage drop across the respective resistor 19a or 19b so that a corresponding voltage pulse is applied via the respective capacitor 20a or 20b to corresponding preamplifiers 21a and 21b which are preferably constructed as cathode followers, or, if transistorized, as emitter-followers. From the preamplifiers the amplified voltage pulses adjusted in well-known manner to the cable impedance are applied to the connecting cables 22a and 22b respectively which may have any desired length in view of the above mentioned adjustment. From the above mentioned cables the signals are applied to the main amplifiers 23a and 23b, respectively, which have in practical embodiments of the invention an amplification factor of 1,000 to 10,000. The outputs of the main amplifiers 23a and 23b are connected to the above mentioned coincidence stage 24 which may be equipped in conventional manner with a coincidence hexode with coincidence transistors and which is designed to deliver as output signals into line 25 only such signals which are applied to the coincidence stage 24 from the main amplifiers 23a and 23b absolutely simultaneously. The output signals of the coincidence stage 24 are delivered to an output stage 26. To the left and to the right of the output stage 26 pulse diagrams are indicated which illustrate signals delivered by the main amplifiers 23a and 23b in relation to time t. In both cases the appearing signals are shown in relation to a reference instant x. It can be seen that the signals 24a and 24b of comparatively large amplitude and resulting from the reception of one of the light pulses emanating from the transmitter station and received by the two separate groups of photocells 17a and 17b appear simultaneously at the coincidence stage 24 and result, therefore, in a clear and strong output signal at the output 27 of the output stage 26. However the irregularly appearing small amplitude signals 24c-24f and constituting the above mentioned "white noise" do not appear simultaneously and consequently are unable to cause in the coincidence stage 24 the output of a corresponding signal. In this manner any influence of general daylight illumination on the reception of the light pulse signals delivered by the transmitter arrangement is safely prevented.

The output signals available at the output 27 may be further processed in various ways.

For instance an adjustable attenuator 28 may be provided by means of which the amplitude of the output signals may be so adjusted that no signal is delivered from the member 28 (or a signal of ineffective amplitude) as long as the visibility is better than a predetermined value thereof so that the pulses of scattered light are comparatively weak. However, when the visibility decreases so that stronger pulses of scattered light impinge on the receiver resulting in correspondingly stronger output signals at 27, then such signals or pulses are passed and delivered to an amplifier 29 from where they may be supplied either to a directly indicating digital voltmeter 40b which may be calibrated directly to ranges of visibility, or they may be applied to a recorder 40a which would continuously record the occurrence of such signals, or finally they may be applied to a relay or similar device 40 which would under such circumstances deliver a control signal. This control signal, in turn, may be used for instance for starting an alarm or warning signal indicating that the range of visibility has descreased below a predetermined level thereof, or for starting the operation of any other desirable device.

The attenuator 28 may also be modified in such a manner that it automatically regulates the amplitude of the output signals appearing at 27 in such a manner that the signals appearing at the input of the amplifier 29 remains constant. In that case the corresponding positions of the regulator member of the attenuator 28 would directly indicate the range of visibility corresponding to the output signals received by the attenuator 28.

Figure 1A:
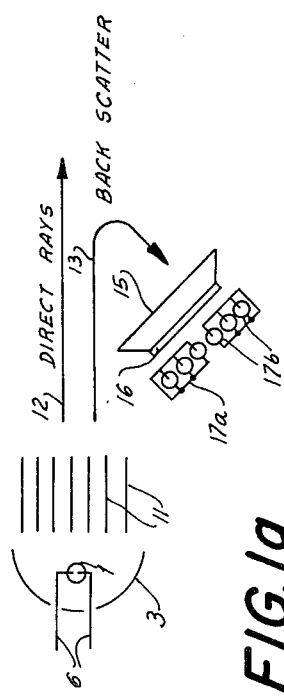
FIG. 1a illustrates diagrammatically a modification of the arrangement according to FIG. 1.

Under certain circumstances it may be desirable and advantageous to modify the arrangement according to FIG. 1 in a manner indicated diagrammatically by FIG. 1a. As can be seen the only difference between FIG. 1 and FIG. 1a is that the receiver arrangement is turned, clockwise as seen in FIG. 1a, through an angle of such 45°. The purpose of this change of orientation of the receiver arrangement is to rely in the reception of light signals only on scatter in backward direction as indicated by the arrow 13. This is advisable if the transmitter-receiver arrangement must be installed in an area where it is impossible to have a representative sample of the medium to be monitored in the immediate vicinity of the transmitter-receiver arrangement. In such case the sample of the medium containing visibility reducing particles may be a certain distance away from the receiver so that forward scatter according to arrow 14 would not be available, while on the other hand substantial amounts of back scatter according to arrow 13 would be effective on the receiver.

In FIG. 1 it will be clear that the coincidence circuit can be considered to constitute a gating circuit with the first of its two inputs constituting a gating-signal input and the second of its two inputs constituting an input to which is applied a signal which is to be passed or not passed. The illustrated circuitry connected to the first input of the coincidence circuit would accordingly constitute means for generating such a gating signal.

Figure 2:
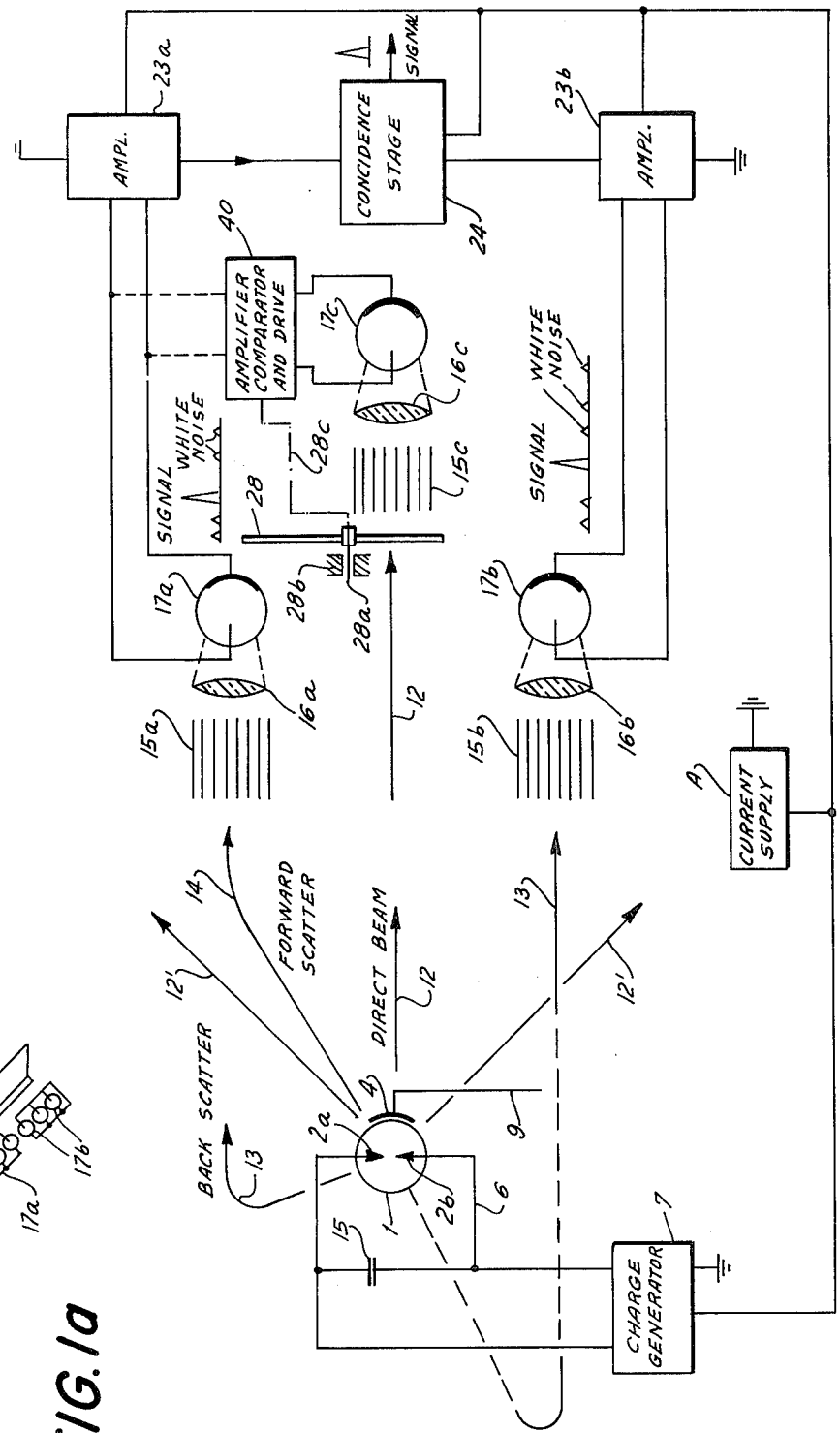
FIG. 2 illustrates another embodiment of the invention.

Referring now to FIG. 2, the embodiment shown therein differs from the embodiments according to FIGS. 1 and 1a first of all in that the transmitter is not unidirectional by means of a reflector or lens system, but is multidirectional or even omni-directional in its radiation output. Otherwise the transmitter components 1, 2, 2a, 2b, 4 and 5-10 are, in this example, analogous to those shown in FIG. 1 and described in reference thereto.

As can be seen from FIG. 2, the spark lamp of the transmitter emits light pulses in a predetermined direction 12 toward the receiver station described further below, but additionally also in other directions as indicated by arrows 12', 13 and 14, these other directions being located within angular spaces on both sides of the direct beam 12. These other directions may include angles up to 180° with the direct beam 12. Although the transmitter is shown without any optical system, it should be understood that optical means may be provided subject to the condition that they permit the radiation of light pulses in said other directions different from the of the direct beam 12.

If the medium, e.g., air, surrounding the transmitter, is substantially free of visibility reducing particles like fog, dust, rain, snow or the like, then light pulses will be transmitted only in the direction of the straight arrows 12 or 12', the latter being only examples of radiation in other directions than that of the direct beam 12. If, however, the medium contains particles causing light scatter then some forward scatter, as indicated e.g. by arrow 14, or back scatter indicated by arrows 13, will occur.

Different from the embodiment of FIGS. 1 and 1a, the receiver station comprises two independent receiver means each composed of at least one photocell 17a and 17b, respectively, a concentrating lens system 16a and 16b respectively, and an arrangement of parallel ducts 15a and 15b, respectively, the latter serving in a well known manner to make the reception of light by the above mentioned receiver means unidirectional. The two above mentioned receiver means are so spaced from each other and so arranged and oriented that they cannot be reached by direct light rays substantially along arrow 12 nor by light rays in direction of the arrows 12', but will be reached by pulses of scatter light arriving in the direction of the arrows 13 or 14 for example.

While in FIG. 2 only one photocell 17a and 17b respectively, is shown for each independent receiver arrangement, it will be understood that a plurality thereof as a group may be provided in each of the receiver means similarly as the groups of photocells 17a and 17b in FIG. 1. The electrical circuitry of the receiver station is otherwise quite analogous to that shown in FIG. 1 as indicated diagrammatically by the amplifiers 23a and 23b and the coincidence stage 24. Other details of the arrangement of the receiver station shown in FIG. 1 are not shown in FIG. 2 only for the purpose of simplifying the illustration. But it should be understood that in this respect the details of the embodiment according to FIG. 1 apply analogously to the embodiment of FIG. 2.

The operation of the embodiment according to FIG. 2 is generally the same as that described in relation to FIG. 1. When pulses of scatter light as illustrated by arrows 13 and 14 reach photocells 17a and 17b, the resulting electrical pulses are applied to the respective amplifiers 23a and 23b and from there to the coincidence stage 24. The output signal is delivered by the coincidence stage 24 only when the above mentioned electrical impulses reach this stage simultaneously. The small pulse diagram placed in FIG. 2 at the right on the photocells 17a and 17b show each a distinct signal resulting from receiving the pulse of scatter light simultaneously by the photocells 17a and 17b and therefore coinciding with each other. In addition, the diagrams show small and irregularly distributed pulses representing the above mentioned "white noise". Since these pulses are comparatively weak and in addition can hardly be expected to coincide exactly, they remain without any effect on the coincidence stage 24 so that in this manner only the intended signals furnished by the photocells appear as single output signals as shown diagrammatically at the right of the coincidence stage 24, while the influence of general daylight or other illumination resulting in "white noise" is entirely eliminated.

The embodiment according to FIG. 2 may be used in various ways. If desired and if conditions permit, the transmitter and receiver stations thereof may be located at a substantial distance from each other without reducing the effectiveness of the arrangement. On the other hand, if desired, the embodiment according to FIG. 2 may be arranged so as to occupy comparatively small space so that the arrangement could be installed for instance aboard ships or even aboard airplanes. As a matter of principle, the arrangement according to FIG. 2 could even be installed wholly or partly within a vessel containing a liquid medium in order to determine analogously the turbidity of the liquid medium or changes thereof.

The embodiment according to FIG. 2 may be supplemented by further receiver means in order to obtain a quantitative measurement of visibility in a medium or, in other words, the degree of light absorption in the medium. For this purpose a further photocell 17c (or a group thereof) together with a lens system 16a and duct system 15c is arranged so as to receive mainly or exclusively light pulses transmitted in the direction of the direct beam 12. A rotatable disc 28 carried by a shaft 28a supported in a bearing 28b is so arranged that it acts as a rotatable filter across the path of the light pulses in direction 12. The transparency of the disc 28 varies in circumferential direction from a maximum to a predetermined minimum, i.e. between various shades of gray so that upon being turned, various portions of the disc 28 position in front of the ducts 15c will suppress to a different degree the illumination of the photocell 17c by direct light pulses arriving along the beam 12. The photocell 17c as well as the photocell 17a are connected to a unit 40 which comprises amplifier, comparator and drive means. The drive means and disc 28 are in operative connection as diagrammatically indicated at 28c for rotating disc 28. The amplifier and comparator means cooperate for comparing the amplitudes of signals furnished by the photocells 17a and 17c, respectively, which means that the amplitude of direct light pulses arriving along arrow 12 is compared with the amplitude of simultaneously arriving pulses of scatter light arriving along arrows 13 or 14 are compared with each other. As long as these amplitiues differ from each other, the disc 28 is further rotated until the amplitudes of the signals delivered by the photocells 17a and 17c are equal to each other. From the position and characteristics of the filter disc 28 at this moment the quantitiative relation between light transmitted directly including losses by scatter and absorption, on one hand, and light transmitted only through scatter can be established. From such an indication conclusions may be drawn concerning the light absorbing or scattering characteristics of particles existing in the respective gaseous or liquid medium.

It can be seen that the arrangement according to the invention is based on the principle of primarily or exclusively detecting the amount of scatter light transmitted through a medium containing visibility reducing particles. Thus, the invention utilizes the phenomenon that the intensity of scatter light increases in proportion with the decrease of visibility. Consequently it is possible to obtain in the arrangement according to the invention comparatively strong signals which are the stronger, the shorter is the range of visibility in the medium. For instance if the range of visibility is cut in half, the corresponding amplitudes of the signals produced at the receiver increase to twice the initial value.

In reference to FIG. 1, the operation of an adjustable attenuator 28 has been described. In certain cases it is advisable to modify this attenuator in such a manner that it operates automatically. In certain cases it is advisable to modify this attenuator in such a manner that it operates automatically. In this case the amplitude of the signal applied to the attenuator is automatically regulated so that the amplitude of the signal delivered by the attenuator is of a predetermined constant value. In this case the condition of the attenuator or the position of a regulating element thereof upon completion of such adjustment would serve immediately as an indication of the amplitude of the signal delivered by the coincidence stage 24, i.e. of the existing range of visibility.

This automatic attenuator system may be further modified in such a manner that it contains first adjustable control circuit means for adjusting the amplitude of the signal as described above and second central circuit means containing a plurality of resistance means for producing a linear relation between the adjusted signal amplitudes and the corresponding range of visibility. The automatic attenuator referred to may have substantially the structure of a well known automatic telephone selector switch with two bands of contacts, one bank forming part of said first control circuit means, the other bank forming part of said second control circuit means. By using this arrangement, it would be possible to arrange matters so that for instance an output signal of one volt would correspond to a visibility of one mile, a voltage of two volts adjusted in another position of the selector switch would correspond to a visibility of two miles, etc. By providing for a linear relation between signal amplitude and range of visibility, it is then possible to use as an indicator a regular digital voltmeter which could be calibrated so as to indicate directly ranges of visibility instead of, or in addition to, volts. This is highly desirable because under these circumstances standard digital meter means of any kind could be used in connection with the arrangement described above.

It should be understood that the arrangement according to FIG. 1a is very satisfactorily operable also if the distance between transmitter and receiver is comparatively large or if the back scatter is constituted by a diffuse reflection by particles present in the respective medium.

In this case one should bear in mind that the transmitter should not be oriented in a direction more or less steeply upward because otherwise reflections by clouds might be received. On the other hand, the transmitter should also not be oriented horizontally because otherwise the light pulse emission of the transmitter could be confused by an observer at a great distance with a beacon. Of course, there may be conditions where just this effect is desired so that light pulses emitted by the spark lamp 1 are intended to serve as a flashing beacon and the arrangement would have the double function of acting both as a beacon and as a fog warning or visibility range determining apparatus. This applies to the arrangements of both FIGS. 1 and 2. Particularly in the case of FIG. 2, the transmitter might be installed for instance on a ship and be visible within a large area. It may even be surrounded by a color filter, e.g., green or red, because the color of the light pulses does not affect the operation of the arrangement described above.

As a matter of fact, the arrangement according to FIG. 2 could be modified in such a manner that the transmitter portion is installed aboard a ship while other ships are equipped with a receiver according to my U.S. Pat. No. 2,941,084. Consequently the two installations working together would serve as an installation warning against collision, and would do this with great efficiency because light pulses from a spark lamp are visible and receivable over much greater distances than other light signals particularly when the range of visibility is comparatively small.

It will be understood that each of the elements described above, or two or more together, may also find a useful application in other types of an arrangement for determining ranges of visibility in a medium differing from the types described above.

While the invention has been illustrated and described as embodied in an arrangement for determining ranges of visibility in a medium by means of the reception of pulses of scatter light, it is not intended to be limited to the details shown, since various modifications and structural changes may be made without departing in any way from the spirit of the present invention.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

What is claimed as new and desired to be protected by Letters Patent is:

1. In an arrangement for measuring atmospheric visibility in fog, in combination, light-projecting means operative for projecting into fog-laden atmosphere in the presence of ambient light a beam of pulsed direct light so that a portion of the light of said beam is scattered by fog droplets and thereby converted into pulsed scattered light while the remainder of the light of said beam stays in the form of pulsed direct light; light receiver means so constructed and arranged relative to said light projecting means that said light receiver means does not receive said direct light but does receive scattered light pulses and also ambient light; signal-generating means connected to said light receiver means and operative for generating an electrical light-indicating signal comprised of pulsed first portions corresponding in amplitude and duration to the intensity and duration of the scattered light pulses received by said receiver means and generated during time intervals corresponding to said scattered light pulses and alternating with second portions corresponding in amplitude and duration to the intensity and duration of the ambient light received by said receiver means during the time intervals intermediate the receipt of successive scattered light pulses and generated during the time intervals intermediate the time intervals corresponding to said scattered light pulses; and indicating means including a visibility indicator calibrated in units of atmospheric visibility, operative for deriving from said light-indicating signal an atmospheric-visibility indication dependent upon the density of said light-scattering fog droplets, said indicating means including suppressing means operative during the time intervals intermediate the receipt by said receiver means of successive scattered light pulses and in dependence upon the light received by said light receiver means but independently of the rate of change of received light for suppressing the effect upon said atmospheric-visibility indication of at least parts of said second portions of said light-indicating signal.

2. In an arrangement as defined in claim 1, wherein said light receiver means is comprised of a first part and a second part, and wherein said signal-generating means and said light-indicating signal respectively constitute first signal-generating means and a first light-indicating signal, and wherein said first signal-generating means is operatively connected to said first part of said light receiver means, and wherein said suppressing means comprise second signal-generating means operatively connected to said second part of said light receiver means and operative for generating a second electrical light-indicating signal comprised of pulsed first portions corresponding in amplitude and duration to the intensity and duration of the scattered light pulses received by said second part of said light receiver means and alternating with second portions corresponding in amplitude and duration to the intensity and duration of the ambient light received by said second part during the time periods intermediate the receipt of successive scattered light pulses, and a coincidence circuit having first and second inputs respectively connected to said first and second signal-generating means for respective receipt of said first and second light-indicating signals and having an output at which is generated a signal corresponding to the signals presented to said first and second inputs when such signals are identical, and means for converting the signal at the output of said coincidence circuit into said atmospheric-visibility indication.

3. An arrangement as defined in claim 1, wherein said suppressing means comprises gating means having an input connected to said signal-generating means for receipt of said light-indicating signal and having a gating-signal input and having an output, and gating-signal-generating means connected to said gating-signal input and operative for furnishing a gating thereto coincidently with receipt by said light receiver means of a scattered light pulse originating from said light-projecting means.

4. In an arrangement as defined in claim 1, wherein said transmitter means include means for confining the light pulses emitted from said transmitter means into a beam of predetermined direction, said confining means comprising a system of ducts arranged in honeycomb fashion extending parallel to each other in said predetermined direction.

5. In an arrangement as defined in claim 1, wherein said light receiver means has an optical axis and is comprised of a photosensitive part and of protective shield means arranged coaxially with said optical axis and operative for preventing direct light from said light-projecting means from reaching said photosensitive part.

6. In an arrangement as defined in claim 5, wherein said axis of said light receiver means extends substantially normal to the direction of said light beam so that light pulses scattered in forward, lateral and backward direction are received through said protective shield means by said receiver means.

7. In an arrangement as defined in claim 5, wherein said axis of said light receiver means includes an acutte angle with the direction of said light beam so that only light pulses scattered in rearward direction are received through said protective shield means by said receiver means.

8. In an arrangement as defined in claim 5, said protective shield means having a light inlet end of a cross section greater than light outlet end thereof, and including light filter means extending transversely through said outlet end.

* * * * *